(12) United States Patent
Hilgren et al.

(10) Patent No.: US 6,514,556 B2
(45) Date of Patent: Feb. 4, 2003

(54) METHOD AND COMPOSITION FOR WASHING POULTRY DURING PROCESSING

(75) Inventors: John D. Hilgren, Shoreview, MN (US); Timothy A. Gutzmann, Eagan, MN (US); Robert D. P. Hei, Baldwin, WI (US)

(73) Assignee: Ecolab Inc., St. Paul, MN (US)

( * ) Notice: Subject to any disclaimer, the term of this patent is extended or adjusted under 35 U.S.C. 154(b) by 0 days.

(21) Appl. No.: 09/738,806

(22) Filed: Dec. 15, 2000

(65) Prior Publication Data

US 2002/0119743 A1 Aug. 29, 2002

(51) Int. Cl.⁷ .................................................. A23B 4/20
(52) U.S. Cl. ........................ 426/652; 426/321; 426/331
(58) Field of Search ........................ 452/71, 173, 81; 119/650, 651, 652; 426/256, 332, 261, 257, 652

(56) References Cited

U.S. PATENT DOCUMENTS

| | | | | |
|---|---|---|---|---|
| 6,028,104 A | * | 2/2000 | Schmidt et al. | 514/557 |
| 6,039,992 A | * | 3/2000 | Compadre et al. | 426/332 |
| 6,103,286 A | * | 8/2000 | Gutzmann et al. | 426/235 |
| 6,113,963 A | * | 9/2000 | Gutzmann et al. | 424/405 |
| 6,183,807 B1 | * | 2/2001 | Gutzmann et al. | 426/321 |
| 6,257,253 B1 | * | 7/2001 | Lentsch et al. | 134/15 |
| 6,302,968 B1 | * | 10/2001 | Baum et al. | 134/15 |

FOREIGN PATENT DOCUMENTS

| | | |
|---|---|---|
| EP | 0 985 349 A2 | 3/2000 |
| WO | WO 93/01716 | 2/1993 |
| WO | WO 94/21122 | 9/1994 |
| WO | WO 94/23575 | 10/1994 |
| WO | WO 99/51095 | 10/1999 |

OTHER PUBLICATIONS

Hilgren, J. et al., *Patent Application*, U.S. patent application Ser. No. 09/614,631, filed Jul. 12, 2000.

Abstract: "Indirect food additives: adjuvants, production aids, and sanitizers", *Fed. Register*, 61(108), 28051–28053, 1 pg. (Jun. 4, 1996).

* cited by examiner

*Primary Examiner*—Charles T. Jordan
*Assistant Examiner*—Judith A. Nelson
(74) *Attorney, Agent, or Firm*—Merchant & Gould P.C.

(57) ABSTRACT

The present invention relates to compositions including peroxyacetic acid and peroxyoctanoic acid and methods for reducing microbial contamination on poultry. The methods include the step of applying a mixed peroxycarboxylic acid composition to poultry.

42 Claims, No Drawings

_US 6,514,556 B2_

METHOD AND COMPOSITION FOR WASHING POULTRY DURING PROCESSING

FIELD OF THE INVENTION

The present invention relates to compositions including peroxyacetic acid and peroxyoctanoic acid and methods for reducing microbial contamination on poultry. The methods include the step of applying a mixed peroxycarboxylic acid composition to poultry.

BACKGROUND OF THE INVENTION

All poultry carcasses entering the processing environment are contaminated with bacteria, some with pathogenic bacteria such as Salmonella. Fecal matter and dirt are the main sources of this contamination. As a result of such contamination, poultry is typically washed at any of several steps during the process of converting a live bird to an edible food product. Such washing aims to remove dirt, offal, blood, viscera, other debris, and microbes from the poultry. Removing or reducing microbes aids the safe storage and consumption of poultry, yet many existing washing procedures fail to significantly reduce the microbe burden on poultry. The potential for poultry skin to become cross-contaminated is worsened by the ability of all types of bacteria (Gram-positive, Gram-negative, flagellated, non-flagellated, rods or cocci) to adhere within only 15 seconds of contact. Once in the processing environment, a significant number of carcasses can become cross-contaminated with pathogens during handling, scalding, mechanical processing, and chilling. Current methods for many of these procedures also fail to significantly reduce the microbe burden on poultry.

Water used for washing or these other procedures is often used repeatedly over time, which provides yet another opportunity spreading, rather than reducing, microbial burden on poultry. For example, the water becomes contaminated with organic matter and microbes from the poultry, and the organic matter provides nutrients for microbial growth in the water over time or through additional use. These microbes can grow on and contaminate additional poultry and processing equipment. In particular, water left untreated in a submersion bath tends to decontaminate poultry early in a shift but contaminates poultry later in the shift. In fact, such water has been identified as a potential source of coliform, _E. coli_ and Salmonella contamination or cross contamination during poultry processing. Salmonella and other microorganisms are generally undesirable to the poultry, the water, and can cause buildup on all water contact surfaces of slime or biofilm, which requires frequent cleaning to remove.

Microbial contamination or cross contamination of poultry via water continues to be a major concern for poultry processors and end users. Although washing, cooling, or heating poultry carcasses with water can reduce potential contamination, the processing water can also serve as a source of contamination or cross contamination. If pathogenic microorganisms in water are not removed, inactivated or otherwise controlled, they can spread to other poultry, potentially contaminating them. Further, handling or processing steps that pool many individual poultry parts tend to increase the risk that a single contaminated item may contaminate the entire lot. Immersing or spray-washing poultry in fresh water can help reduce surface populations of microorganisms. However sterilization by repeated washing, even with sterile water, cannot be achieved because microorganisms within tissues of poultry remain in place.

The addition of antimicrobial agents to wash or process water can inactivate vegetative bacteria cells in water, helping avoid contamination. Ideally, an antimicrobial agent or compound used in such a system will have several important properties in addition to its antimicrobial efficacy. The compound or agent should have no technical effect on the final food product. Residual activity implies the presence of a film of antimicrobial material which will continue to have antimicrobial effect which may require further rinsing of the food product. The antimicrobial agent preferably should also be odor free to prevent transfer of undesirable odors onto food stuffs. If direct food contact occurs, the antimicrobial agent should also be composed of food additive materials which will not affect food wholesomeness, nor affect humans should incidental ingestion result. In addition, the antimicrobial agent should preferably be composed of naturally occurring or innocuous ingredients, which are chemically compatible with the environment and cause no concerns for toxic residues within the water.

In the past, poultry wash or process waters have generally been treated with chlorinated compounds, organic acids, acidified sodium chlorite, trisodium phosphate, or ozone. Generally, these materials are effective in reducing microbial contamination on poultry. However, the use rate of these antimicrobials is very high because they are not effective at low concentrations or they tend to be rapidly consumed by the high organic load included with the poultry. Excessive chlorination of food processing water with hypochlorite has prompted concern over production of toxic or carcinogenic organochlorine compounds and other by-products.

Further, the efficacy of conventional antimicrobial agents on the surface of poultry is often limited. For example, it has been reported that, generally, concentrations of more than 4 wt-% of organic acids or of 5 to 10 wt-% of trisodium phosphate are required to effectively reduce contamination of poultry skin by _S. typhimurium_. Antimicrobial agents such as peroxides or lactic acid can result in discoloring, bleaching, or bloating of poultry tissue.

The EPA approved a peroxyacetic acid-based composition in 1996 for controlling microbial growth and reducing biofilm formation in fruit and vegetable transport or process waters. From a historical perspective, peroxyacetic acid has been used for food contact surface sanitizing, aseptic packaging and medical device cold-sterilization. In addition to its biocidal properties, the environmentally-friendly decomposition byproducts and good stability in the presence of organic matter helped gain acceptance of this technology among fruit and vegetable packers, handlers, and processors.

Nevertheless, there remains a need for improved antimicrobial compositions for addition to waters used for washing or processing poultry.

SUMMARY OF THE INVENTION

The present invention relates to compositions including peroxyacetic acid and peroxyoctanoic acid and methods for reducing microbial contamination on poultry. The methods include the step of applying a mixed peroxycarboxylic acid composition to poultry. The compositions and methods of the invention provide an antimicrobial agent useful in water for washing or processing poultry, that has a high degree of antimicrobial efficacy, and that is safely ingestible by humans while imposing no unacceptable environmental incompatibility.

A preferred antimicrobial composition of the present invention includes acetic acid, octanoic acid, peroxyacetic acid, peroxyoctanoic acid, and hydrogen peroxide. In one embodiment, an antimicrobial concentrate composition of the present invention includes about 40 to about 70 weight-% acetic acid, about 2 to about 20 weight-% octanoic acid, and about 5 to about 15 weight-% hydrogen peroxide. In another embodiment, the antimicrobial concentrate composition of the present invention includes an equilibrium mixture resulting from a combination of about 40 to about 70 weight-% acetic acid, about 2 to about 20 weight-% octanoic acid, and about 5 to about 15 weight-% hydrogen peroxide. In a third embodiment, the antimicrobial concentrate composition of the present invention includes about 30 to about 60 weight-% acetic acid, about 1 to about 15 weight-% octanoic acid, about 2 to about 12 weight-% hydrogen peroxide, about 6 to about 16 weight-% peroxyacetic acid, and about 0.1 to about 5 weight-% peroxyoctanoic acid.

In one embodiment, an antimicrobial use composition of the invention includes about 5 to about 1000 ppm acetic acid, about 0.5 to about 100 ppm octanoic acid, about 1 to about 200 ppm hydrogen peroxide, about 2 to about 300 ppm peroxyacetic acid, and about 0.1 to about 20 ppm peroxyoctanoic acid.

The compositions of the invention and other mixed peroxycarboxylic acid antimicrobial compositions can be employed in methods for reducing microbial contamination on poultry and in water used for washing or processing poultry. Preferred mixed peroxycarboxylic acid antimicrobial compositions for use in the methods of the invention include mixtures of peroxyacetic acid and peroxyoctanoic acid in either liquid or gaseous form. These methods include applying to the poultry during processing a mixed peroxycarboxylic acid antimicrobial composition, preferably in an amount and time sufficient to reduce the microbial population. The composition can be applied by methods including submersing, rinsing, spraying, or air chilling the poultry, or a combination of these routes. During processing, the composition can be applied to whole, dismembered, portioned, or boned poultry.

In one embodiment of the method of the invention, the method includes recovering a mixed peroxycarboxylic acid antimicrobial composition previously applied to poultry. The recovered composition can be treated by adding a sufficient amount of a mixture of peroxycarboxylic acids to yield a recycled mixed peroxycarboxylic acid antimicrobial composition. The recycled mixed composition includes a reduced level of microbes, such as human pathogens, and can be disposed of more safely. Alternatively, the recycled mixed composition can be applied to poultry during processing. Preferably, the mixture of peroxycarboxylic acids added to form the recycled composition is formed by adding a concentrate composition of peroxyacetic acid and peroxyoctanoic acid to form a composition with suitable use antimicrobial levels of these peroxycarboxylic acids.

The compositions can include peroxyheptanoic and/or peroxynonanoic acid in place of or in addition to peroxyoctanoic acid.

DETAILED DESCRIPTION OF THE INVENTION

Definitions

As used herein the term "poultry" refers to all forms of any bird kept, harvested, or domesticated for meat or eggs, and including chicken, turkey, ostrich, game hen, squab, guinea fowl, pheasant, quail, duck, goose, emu, or the like and the eggs of these birds. Poultry includes whole, sectioned, processed, cooked or raw poultry, and encompasses all forms of poultry flesh, by-products, and side products. The flesh of poultry includes muscle, fat, organs, skin, bones and body fluids and like components that form the animal. Forms of animal flesh include, for example, the whole or part of animal flesh, alone or in combination with other ingredients. Typical forms include, for example, processed poultry meat, such as cured poultry meat, sectioned and formed products, minced products, finely chopped products and whole products.

As used herein, the terms "mixed" or "mixture" when used relating to "peroxycarboxylic acid composition" or "peroxycarboxylic acids" refer to a composition or mixture including more than one peroxycarboxylic acid, such as a composition or mixture including peroxyacetic acid and peroxyoctanoic acid.

As used herein, the phrase "poultry debris" refers to any debris, residue, material, dirt, offal, poultry part, poultry waste, poultry viscera, poultry organ, fragments or combinations of such materials, and the like removed from a poultry carcass or portion during processing and that enters a waste stream.

As used herein, the phrase "densified fluid" refers to a fluid in a critical, subcritical, near critical, or supercritical state. The fluid is generally a gas at standard conditions of one atmosphere pressure and 0° C. As used herein, the phrase "supercritical fluid" refers to a dense gas that is maintained above its critical temperature, the temperature above which it cannot be liquefied by pressure. Supercritical fluids are typically less viscous and diffuse more readily than liquids. Preferably a densified fluid is at, above, or slightly below its critical point. As used herein, the phrase "critical point" is the transition point at which the liquid and gaseous states of a substance merge into each other and represents the combination of the critical temperature and critical pressure for a substance. The critical pressure is a pressure just sufficient to cause the appearance of two phases at the critical temperature. Critical temperatures and pressures have been reported for numerous organic and inorganic compounds and several elements.

As used herein, the terms "near critical" fluid or "subcritical" fluid refer to a fluid material that is typically below the critical temperature of a supercritical fluid, but remains in a fluid state and denser than a typical gas due to the effects of pressure on the fluid. Preferably a subcritical or near critical fluid is at a temperature and/or pressure just below its critical point. For example, a subcritical or near critical fluid can be below its critical temperature but above its critical pressure, below its critical pressure but above its critical temperature, or below both its critical temperature and pressure. The terms near critical and subcritical do not refer to materials in their ordinary gaseous or liquid state.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about", the claims include equivalents to the quantities.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can effect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition.

For the purpose of this patent application, successful microbial reduction is achieved when the microbial populations are reduced by at least about 50%, or by significantly more than is achieved by a wash with water. Larger reductions in microbial population provide greater levels of protection for processed poultry product.

As used herein, a composition or combination "consisting essentially" of certain ingredients refers to a composition including those ingredients and lacking any ingredient that materially affects the basic and novel characteristics of the composition or method. The phrase "consisting essentially of" excludes from the claimed compositions and methods: a coupling agent; an ingredient that cannot be employed in food products or in food wash, handling, or processing according to U.S. government rules or regulations; and/or a peroxycarboxylic acid or carboxylic acid with 10 or more carbon atoms; unless such an ingredient is specifically listed after the phrase.

Peroxycarboxylic Acid Antimicrobial Composition
Compositions of Carboxylic Acids and Peroxycarboxylic Acids Among other constituents, the composition of the present invention includes a carboxylic acid. Generally, carboxylic acids have the formula R—COOH wherein the R can represent any number of different groups including aliphatic groups, alicyclic groups, aromatic groups, heterocyclic groups, all of which can be saturated or unsaturated as well as substituted or unsubstituted. Carboxylic acids can have one, two, three, or more carboxyl groups. The composition and methods of the invention can employ carboxylic acids containing as many as 18 carbon atoms. Examples of suitable carboxylic acids include formic, acetic, propionic, butanoic, pentanoic, hexanoic, heptanoic, octanoic, nonanoic, decanoic, undecanoic, dodecanoic, lactic, maleic, ascorbic, citric, hydroxyacetic, neopentanoic, neoheptanoic, neodecanoic, oxalic, malonic, succinic, glutaric, adipic, pimelic and subric acid. Carboxylic acids which are generally useful are those having one or two carboxyl groups where the R group is a primary alkyl chain having a length of $C_2$ to $C_{12}$. The primary alkyl chain is that carbon chain of the molecule having the greatest length of carbon atoms and directly appending carboxyl functional groups. Octanoic acid can reduce surface tension to assist in wetting of hydrophobic surfaces like poultry skin.

Peroxycarboxylic (or percarboxylic) acids generally have the formula $R(CO_3H)_n$, where R is an alkyl, arylalkyl, cycloalkyl, aromatic or heterocyclic group, and n is one, two, or three, and named by prefixing the parent acid with peroxy. While peroxycarboxylic acids are not as stable as carboxylic acids, their stability generally increases with increasing molecular weight. Thermal decomposition of these acids can generally proceed by free radical and nonradical paths, by photodecomposition or radical-induced decomposition, or by the action of metal ions or complexes. Percarboxylic acids can be made by the direct, acid catalyzed equilibrium action of hydrogen peroxide with the carboxylic acid, by autoxidation of aldehydes, or from acid chlorides, and hydrides, or carboxylic anhydrides with hydrogen or sodium peroxide.

Peroxycarboxylic acids useful in the compositions and methods of the present invention include peroxyformic, peroxyacetic, peroxypropionic, peroxybutanoic, peroxypentanoic, peroxyhexanoic, peroxyheptanoic, peroxyoctanoic, peroxynonanoic, peroxydecanoic, peroxyundecanoic, peroxydodecanoic, peroxylactic, peroxymaleic, peroxyascorbic, peroxyhydroxyacetic, peroxyoxalic, peroxymalonic, peroxysuccinic, peroxyglutaric, peroxyadipic, peroxypimelic and peroxysubric acid and mixtures thereof. Peroxy forms of carboxylic acids with more than one carboxylate moiety can have one or more of the carboxyl moieties present as peroxycarboxyl moieties. These peroxycarboxylic acids have been found to provide good antimicrobial action with good stability in aqueous mixtures. In a preferred embodiment, the composition of the invention utilizes a combination of several different peroxycarboxylic acids. Preferably, the composition includes one or more small $C_2$–$C_4$ peroxycarboxylic acids and one or more large $C_7$–$C_9$ peroxycarboxylic acids. Especially preferred is an embodiment in which the small peroxycarboxylic acid is peroxyacetic acid and the large acid is peroxyoctanoic acid.

Typically, the compositions and methods of the present invention include peroxyacetic acid. Peroxyacetic (or peracetic) acid is a peroxycarboxylic acid having the formula: $CH_3COOOH$. Generally, peroxyacetic acid is a liquid having an acrid odor at higher concentrations and is freely soluble in water, alcohol, ether, and sulfuric acid. Peroxyacetic acid can be prepared through any number of methods known to those of skill in the art including preparation from acetaldehyde and oxygen in the presence of cobalt acetate. A solution of peroxyacetic acid can be obtained by combining acetic acid with hydrogen peroxide. A 50% solution of peroxyacetic acid can be obtained by combining acetic anhydride, hydrogen peroxide and sulfuric acid. Other methods of formulation of peroxyacetic acid include those disclosed in U.S. Pat. No. 2,833,813, which is incorporated herein by reference.

Typically, the compositions and methods of the present invention include peroxyoctanoic acid, peroxynonanoic acid, or peroxyheptanoic acid, preferably peroxyoctanoic acid. Peroxyoctanoic (or peroctanoic) acid is a peroxycarboxylic acid having the formula, for example, of n-peroxyoctanoic acid: $CH_3(CH_2)_6COOOH$. Peroxyoctanoic acid can be an acid with a straight chain alkyl moiety, an acid with a branched alkyl moiety, or a mixture thereof. Peroxyoctanoic acid can be prepared through any number of methods known to those of skill in the art. A solution of peroxyoctanoic acid can be obtained by combining octanoic acid and hydrogen peroxide.

A preferred antimicrobial composition of the present invention includes acetic acid, octanoic acid, peroxyacetic acid, and peroxyoctanoic acid. Such a composition can also include a chelating agent. A preferred composition preferably includes a combination of peroxyacetic acid and peroxyoctanoic acid effective for killing one or more of the food-borne pathogenic bacteria associated with poultry, such as *Salmonella typhimurium, Campylobacter jejuni, Listeria monocytogenes,* and *Escherichia coli* O157:H7, and the like. The compositions and methods of the present invention have activity against a wide variety of microorganisms such as Gram positive (for example, *Listeria monocytogenes*) and Gram negative (for example, *Escherichia coli*) bacteria, yeast, molds, bacterial spores, viruses, etc. The compositions and methods of the present invention, as described above, have activity against a wide variety of human pathogens. The compositions and methods can kill a wide variety of microbes on the surface of a poultry or in water used for washing or processing of poultry.

The preferred compositions include concentrate compositions and use compositions. Typically, an antimicrobial concentrate composition can be diluted, for example with water, to form an antimicrobial use composition. In a preferred embodiment, the concentrate composition is diluted into water employed for washing or processing poultry.

Liquid Peroxycarboxylic Acid Antimicrobial Composition

A preferred antimicrobial concentrate composition of the present invention includes about 40 to about 70 weight-%, preferably about 45 to about 65 weight-%, preferably about 50 to about 60 weight-% acetic acid; about 2 to about 20 weight-%, preferably about 2 to about 8 weight-% octanoic acid; and about 5 to about 15 weight-% hydrogen peroxide. This composition can advantageously also include about 0.3 to about 1 weight-% chelating agent. Preferably, such an antimicrobial concentrate composition includes about 55 weight-% acetic acid, about 11 weight-% hydrogen peroxide, and about 4 weight-% octanoic acid. This composition can advantageously also include about 0.6 weight-% chelating agent. This concentrate composition can be prepared according to the proportions described above. After combining the ingredients in these proportions, certain ingredients, such as the acetic acid, octanoic acid, and hydrogen peroxide, react to form peroxyacetic acid and peroxyoctanoic acid.

By about two weeks after combining, the reaction of these ingredients has approached equilibrium. That is, the relative amounts of one or more of peroxyacetic acid, acetic acid, peroxyoctanoic acid, octanoic acid, and hydrogen peroxide will be roughly constant. The equilibrium amount will be affected by decomposition or other reaction, if any, of any labile species. A preferred antimicrobial concentrate composition of the present invention includes an equilibrium mixture resulting from a combination of about 40 to about 70 weight-%, preferably about 45 to about 65 weight-%, preferably about 50 to about 60 weight-% acetic acid; about 2 to about 20 weight-%, preferably about 2 to about 8 weight-% octanoic acid; and about 5 to about 15 weight-% hydrogen peroxide. This equilibrium composition can advantageously also include about 0.3 to about 1 weight-% chelating agent. A more preferred antimicrobial concentrate composition of the present invention includes an equilibrium mixture resulting from a combination of about 55 weight-% acetic acid, about 11 weight-% hydrogen peroxide, and about 4 weight-% octanoic acid. This equilibrium composition can advantageously also include about 0.6 weight-% chelating agent.

A preferred antimicrobial concentrate composition of the present invention includes about 30 to about 60 weight-%, preferably about 35 to about 60 weight-%, preferably about 35 to about 50 weight-%, preferably about 40 to about 50 weight-% acetic acid; about 1 to about 15 weight-%, preferably about 1 to about 7 weight-% octanoic acid; about 2 to about 12 weight-%, preferably about 2 to about 8 weight-% hydrogen peroxide; about 6 to about 16 weight-%, preferably about 8 to about 16 weight-% peroxyacetic acid; and about 0.1 to about 5 weight-%, preferably about 0.1 to about 2 weight-% peroxyoctanoic acid. This concentrate composition can advantageously also include about 0.1 to about 2 weight-% chelating agent. Preferably, such an antimicrobial concentrate composition includes about 40 weight-% acetic acid, about 3 weight-% octanoic acid, about 6 weight-% hydrogen peroxide, about 10 weight-% peroxyacetic acid, and about 0.8 weight-% peroxyoctanoic acid. This antimicrobial concentrate composition can advantageously include about 0.6 weight-% chelating agent. Preferably, such an antimicrobial concentrate composition includes about 41 weight-% acetic acid, about 3.2 weight-% octanoic acid, about 6.2 weight-% hydrogen peroxide, about 12 weight-% peroxyacetic acid, and about 0.80 weight-% peroxyoctanoic acid. This antimicrobial concentrate composition can advantageously include about 0.60 weight-% chelating agent. These preferred compositions can be produced by mixing the acid and peroxide components at proportions listed in preceding paragraphs and allowing the composition to sit at ambient temperature for a period of about one to about two weeks. That is, these preferred compositions can be considered equilibrium compositions.

The compositions of the present invention also include antimicrobial use compositions. Preferred antimicrobial use compositions include about 5 to about 1000 ppm acetic acid; about 0.5 to about 100 ppm, preferably about 0.5 to about 75 ppm octanoic acid; about 1 to about 200 ppm, preferably about 1 to about 110 ppm hydrogen peroxide; about 2 to about 300 ppm, preferably about 2 to about 220 ppm peroxyacetic acid, and about 0.1 to about 20 ppm peroxyoctanoic acid. Such a use composition can advantageously include about 0.05 to about 30 ppm chelating agent. Preferably, such an antimicrobial use composition includes about 7 (e.g., 6.8) ppm acetic acid, about 0.5 ppm octanoic acid, about 1 ppm hydrogen peroxide, about 2 ppm peroxyacetic acid, and about 0.1 ppm peroxyoctanoic acid. This use composition can advantageously include about 0.1 ppm chelating agent. Preferably, such an antimicrobial use composition includes about 20 (e.g. 17) ppm acetic acid, about 1 to about 2 (e.g., 1.3) ppm octanoic acid, about 2 to about 3 (e.g., 2.6) ppm hydrogen peroxide, about 5 ppm peroxyacetic acid, and about 0.3 ppm peroxyoctanoic acid. This use composition can advantageously include about 0.3 ppm chelating agent. Preferably, such an antimicrobial use composition includes about 100 (e.g., 101) ppm acetic acid, about 8 ppm octanoic acid, about 10 to about 20 (e.g., 16) ppm hydrogen peroxide, about 30 ppm peroxyacetic acid, and about 2 ppm peroxyoctanoic acid. This use composition can advantageously include about 1 to about 2 (e.g. 1.5) ppm chelating agent. Preferably, such an antimicrobial use composition includes about 1000 (e.g. 985) ppm acetic acid, about 70 to about 80 (e.g. 74) ppm octanoic acid, about 100 to about 200 (e.g. 110) ppm hydrogen peroxide, about 220 (e.g., 213) ppm peroxyacetic acid, and about 10 to about 20 (e.g. 14) ppm peroxyoctanoic acid. This use composition can advantageously include about 10 to about 20 (e.g., 13) ppm chelating agent. Different dilutions of a concentrate composition can result in different levels of the components of the use composition, generally maintaining the relative proportions. For example, a use composition of the present invention can have concentrations twice, one half, or one quarter those listed above.

More About Liquid Peroxycarboxylic Acid Compositions

The level of reactive species, such as peroxy acids and/or hydrogen peroxide, in a use composition can be affected, typically diminished, by organic matter that is found in or added to the use composition. For example, when the use composition is a bath or spray used for washing poultry, poultry organic matter or accompanying organic matter will consume peroxy acid and peroxide. Thus, the present amounts of ingredients in the use compositions refer to the composition before or early in use, with the understanding that the amounts will diminish as organic matter is added to the use composition.

In addition, the concentrate and use compositions change with age. It is believed that in approximately one year at ambient conditions the amount of peroxycarboxylic acid in the compositions can decrease to about 70% to about 80%, preferably about 80% to about 85%, of the initial equilibrium values or use composition levels. Such aged compositions are included in the scope of the present invention.

In each of the compositions described above, the chelating agent is an optional, but preferred, ingredient. Typically the balance of each of the compositions described above is made up primarily or exclusively of a solvent, such as water, e.g. tap or other potable water.

The compositions of the present invention preferably include only ingredients that can be employed in poultry products or in poultry wash, handling, or processing, for example, according to government (e.g. FDA or USDA) rules and regulations. Preferably, the composition is free of any peroxycarboxylic acid or carboxylic acid with 10, 12, or more carbon atoms. Such 10, 12, or more carbon acids can impart undesirable residues (e.g. bad tasting and/or malodorous) to poultry.

Each of the compositions listed above can be formulated by combining each of the listed ingredients. In addition, certain compositions including both acid and peroxy acid can be formulated by combining the acids and hydrogen peroxide, which forms peroxy acids. Typically, the pH of an equilibrium mixture is less than about 1 or about 2, and the pH of a 1% solution of the equilibrium mixture in water is about 2 to about 7, depending on the other components of the 1% solution, and the pH of a use composition can be from about 4 to about 7 depending on the other components.

Other Fluid Compositions

The present methods can employ antimicrobial compositions including a critical, near critical, or supercritical (densified) fluid and an antimicrobial agent or a gaseous composition of an antimicrobial agent. The densified fluid can be a near critical, critical, supercritical fluid, or another type of fluid with properties of a supercritical fluid. Fluids suitable for densification include carbon dioxide, nitrous oxide, ammonia, xenon, krypton, methane, ethane, ethylene, propane, certain fluoroalkanes (e.g., chlorotrifluoromethane and monofluoromethane), and the like, or mixtures thereof. Preferred fluids include carbon dioxide. The antimicrobial composition can also include other ingredients, such as another fluid or gas; a carrier, solvent or cosolvent; an oxidizing agent; a fatty acid; or a mixture thereof.

The antimicrobial agent applied with a densified fluid system can be any of a variety of food surface compatible antimicrobial agents, such as one or more peroxycarboxylic acids, quaternary ammonium antimicrobial agents, acid sanitizers, mixtures thereof, and other food surface compatible antimicrobial agents. A preferred densified fluid antimicrobial composition that can be employed in the present methods includes densified carbon dioxide, peroxyacetic acid, hydrogen peroxide, acetic acid, peroxyoctanoic acid, and octanoic acid, which can be referred to as a densified fluid mixed peroxycarboxylic acid composition.

In another embodiment, the antimicrobial composition includes the fluid, an antimicrobial agent, and any of the optional or added ingredients, but is in the form of a gas.

Densified fluid antimicrobial compositions can be applied by any of several methods known to those of skill in the art. Such methods include venting at the poultry carcass or part a vessel containing densified fluid and antimicrobial agent. The aqueous phase, which includes hydrogen peroxide, is advantageously retained in the device. The vented gas includes an effective amount of antimicrobial agent making the densified fluid peroxycarboxylic acid compositions effective antimicrobial agents.

Because of the high pressure nature of the densified fluid compositions of the invention, these compositions are typically applied by venting a vessel containing the composition through a pressure relief device that is designed to promote rapid efficient coverage of the poultry carcass or part. Devices including such a pressure relief device include sprayers, foggers, foamers, foam pad applicators, brush applicators or any other device that can permit the expansion of the fluid materials from high pressure to ambient pressure while applying the material to the poultry carcass or part.

The densified fluid peroxycarboxylic acid composition can also be applied to poultry by any of a variety of methods known for applying gaseous agents to poultry during processing, including air chilling and packaging (e.g. modified atmosphere packaging), particularly at steps where adding water to the poultry is disadvantageous. Other points in poultry processing suitable for application of a gaseous peroxycarboxylic acid composition include any step including inert atmosphere processing, carbon dioxide stunning, and the like.

Densified fluid antimicrobial compositions can be made by reacting an oxidizable substrate with an oxidizing agent in a medium comprising a densified fluid to form an antimicrobial composition. This reaction is typically carried out in a vessel suitable for containing a densified fluid. Reacting can include adding to the vessel the oxidizable substrate and the oxidizing agent, and adding fluid to the vessel to form the densified fluid. A preferred reaction system involves a reaction between a carboxylic acid and hydrogen peroxide to form the corresponding peroxycarboxylic acid. The hydrogen peroxide is commonly supplied in the form of an aqueous solution of hydrogen peroxide. Preferred carboxylic acids include acetic acid, heptanoic acid, octanoic acid, nonanoic acid, and mixtures thereof.

Supercritical, subcritical, near supercritical, and other dense fluids and solvents that can be employed with such fluids are disclosed in U.S. Pat. No. 5,306,350, issued Apr. 26, 1994 to Hoy et al., which is incorporated herein for such disclosure. Supercritical and other dense forms of carbon dioxide, and cosolvents, co-surfactants, and other additives that can be employed with these forms of carbon dioxide are disclosed in U.S. Pat. No. 5,866,005, issued Feb. 2, 1999 to DeSimone et al., which is incorporated herein for such disclosure.

Hydrogen Peroxide

The antimicrobial composition of the invention typically also include a hydrogen peroxide constituent. Hydrogen peroxide in combination with the percarboxylic acid provides certain antimicrobial action against microorganisms. Additionally, hydrogen peroxide can provide an effervescent action which can irrigate any surface to which it is applied. Hydrogen peroxide works with a mechanical flushing action once applied which further cleans the surface of application. An additional advantage of hydrogen peroxide is the food compatibility of this composition upon use and decomposition. For example, combinations of peroxyacetic acid, peroxyoctanoic acid, and hydrogen peroxide result in acetic acid, octanoic acid, water, and oxygen upon decomposition, all of which are food product compatible.

Many oxidizing agents can be used for generating peroxycarboxylic acids. Suitable oxidizing agents, in addition to hydrogen peroxide, include perborate, percarbonate, and persulfate. Hydrogen peroxide is generally preferred for several reasons. After application of the $H_2O_2$/peroxycarboxylic acid germicidal agent, the residue left merely includes water and an acidic constituent. Deposition of these products on the surface of a poultry processing apparatus, such as a bath or spray apparatus, will not adversely effect the apparatus, the handling or processing, or the poultry washed therein.

Hydrogen peroxide ($H_2O_2$), has a molecular weight of 34.014 and it is a weakly acidic, clear, colorless liquid. The four atoms are covalently bonded in a H—O—O—H structure. Generally, hydrogen peroxide has a melting point of −0.41° C., a boiling point of 150.2° C., a density at 25° C. of 1.4425 grams per $cm^3$, and a viscosity of 1.245 centipoise at 20° C.

Carrier

The composition of the invention also includes a carrier. The carrier provides a medium which dissolves, suspends, or carries the other components of the composition. For example, the carrier can provide a medium for solubilization and production of peroxycarboxylic acid and for forming an equilibrium mixture. The carrier also functions to deliver and wet the antimicrobial composition of the invention to the poultry. To this end, the carrier may contain any component or components that can facilitate these functions.

Generally, the carrier includes primarily water which is an excellent solubilizer and medium for reaction and equilibrium. The carrier can include or be primarily an organic solvent, such as simple alkyl alcohols, e.g., ethanol, isopropanol, n-propanol, and the like. Polyols are also useful carriers, including propylene glycol, polyethyleneglycol, glycerol, sorbitol, and the like. Any of these compounds may be used singly or in combination with other organic or inorganic constituents or, in combination with water or in mixtures thereof.

Generally, the carrier makes up a large portion of the composition of the invention and may be the balance of the composition apart from the active antimicrobial components, adjuvants, and the like. Here again, the carrier concentration and type will depend upon the nature of the composition as a whole, the environmental storage, and method of application including concentration of the antimicrobial agent, among other factors. Notably the carrier should be chosen and used at a concentration which does not inhibit the antimicrobial efficacy of the active agent in the composition of the invention.

Adjuvants

The antimicrobial composition of the invention can also include any number of adjuvants. Specifically, the composition of the invention can include stabilizing agents, wetting agents, hydrotropes, thickeners, a surfactant, foaming agents, acidifiers, as well as pigments or dyes among any number of constituents which can be added to the composition. Such adjuvants can be preformulated with the antimicrobial composition of the invention or added to the system simultaneously, or even after, the addition of the antimicrobial composition. The composition of the invention can also contain any number of other constituents as necessitated by the application, which are known to those of skill in the art and which can facilitate the activity of the present invention.

Stabilizing Agents

Stabilizing agents can be added to the composition of the invention, for example, to stabilize the peracid and hydrogen peroxide and prevent the premature oxidation of this constituent within the composition of the invention.

Chelating agents or sequestrants generally useful as stabilizing agents in the present compositions include alkyl diamine polyacetic acid-type chelating agents such as EDTA (ethylene diamine tetraacetate tetrasodium salt), acrylic and polyacrylic acid-type stabilizing agents, phosphonic acid, and phosphonate-type chelating agents among others. Preferable sequestrants include phosphonic acids and phosphonate salts including 1-hydroxy ethyldene-1,1-diphosphonic acid ($CH_3C(PO_3H_2)_2OH$) (HEDP), amino[tri(methylene phosphonic acid)] ($[CH_2PO_3H_2]_2$(ethylene diamine[tetra methylene-phosphonic acid)], 2-phosphene butane-1,2,4-tricarboxylic acid, as well as the alkyl metal salts, ammonium salts, or alkyloyl amine salts, such as mono, di, or tetra-ethanolamine salts. The stabilizing agent is used in a concentration ranging from about 0 weight percent to about 20 weight percent of the composition, preferably from about 0.1 weight percent to about 10 weight percent of the composition, and most preferably from about 0.2 weight percent to 5 weight percent of the composition.

Amino phosphates and phosphonates are also suitable for use as chelating agents in the compositions of the invention and include ethylene diamine (tetramethylene phosphonates), nitrilotrismethylene phosphates, diethylenetriamine (pentamethylene phosphonates). These amino phosphonates commonly contain alkyl or alkaline groups with less than 8 carbon atoms. The phosphonic acid may also include a low molecular weight phosphonopolycarboxylic acid such as one having about 2–4 carboxylic acid moieties and about 1–3 phosphonic acid groups. Such acids include 1-phosphono-1-methylsuccinic acid, phosphonosuccinic acid and 2-phosphonobutane-1,2,4-tricarboxylic acid.

Commercially available food additive chelating agents include phosphonates sold under the trade name DEQUEST® including, for example, 1-hydroxyethylidene-1,1-diphosphonic acid, available from Monsanto Industrial Chemicals Co., St. Louis, Mo., as DEQUEST®2010; amino (tri(methylenephosphonic acid)), ($N[CH_2PO_3H_2]_3$), available from Monsanto as DEQUEST® 2000; ethylenediamine [tetra(methylenephosphonic acid)] available from Monsanto as DEQUEST® 2041; and 2-phosphonobutane-1,2,4-tricarboxylic acid available from Mobay Chemical Corporation, Inorganic Chemicals Division, Pittsburgh, Pa., as Bayhibit AM.

The above-mentioned phosphonic acids can also be used in the form of water soluble acid salts, particularly the alkali metal salts, such as sodium or potassium; the ammonium salts or the alkylol amine salts where the alkylol has 2 to 3 carbon atoms, such as mono-, di-, or triethanolamine salts. If desired, mixtures of the individual phosphonic acids or their acid salts can also be used.

The concentration of chelating agent useful in the present invention generally ranges from about 0.01 to about 10 wt-%, preferably from about 0.1 to about 5 wt-%, most preferably from about 0.5 to about 2 wt-%.

Wetting or Defoaming Agents

Also useful in the composition of the invention are wetting and defoaming agents. Wetting agents function to increase the surface contact or penetration activity of the antimicrobial composition of the invention. Wetting agents which can be used in the composition of the invention include any of those constituents known within the art to raise the surface activity of the composition of the invention.

Along these lines, surfactants, and especially nonionic surfactants, can also be useful in the present invention. Nonionic surfactants which can be useful in the present invention are those which include ethylene oxide moieties, propylene oxide moieties, as well a mixtures thereof, and ethylene oxide-propylene oxide moieties in either heteric or block formation. Additionally useful in the present invention are nonionic surfactants which include an alkyl ethylene oxide compounds, alkyl propylene oxide compounds, as well as mixtures thereof, and alkyl ethylene oxide-propylene oxide compounds where the ethylene oxide propylene oxide moiety is either in heteric or block formation. Further useful in the present invention are nonionic surfactants having any mixture or combination of ethylene oxide-propylene oxide moieties linked to a alkyl chain where the ethylene oxide and propylene oxide moieties can be in any randomized or ordered pattern and of any specific length. Nonionic surfactants useful in the present invention can also include randomized sections of block and heteric ethylene oxide propylene oxide, or ethylene oxide-propylene oxide, such as ethylene diamine ethylene oxides, ethylene diamine propylene oxides, mixtures thereof, and ethylene diamine EO-PO compounds, including those sold under the tradename Tetronic.

Generally, the concentration of nonionic surfactant used in a composition of the present invention can range from about 0 wt-% to about 5 wt-% of the composition, preferably from about 0 wt-% to about 2 wt-% of the concentrate composition, and most preferably from about 0 wt-% to about 1 wt-% of the composition.

The composition used in the methods of the invention can also contain additional ingredients as necessary to assist in defoaming.

Generally, defoamers which can be used in accordance with the invention include silica and silicones; aliphatic acids or esters; alcohols; sulfates or sulfonates; amines or amides; halogenated compounds such as fluorochlorohydrocarbons; vegetable oils, waxes, mineral oils as well as their sulfated derivatives; fatty acid soaps such as alkali, alkaline earth metal soaps; and phosphates and phosphate esters such as alkyl and alkaline diphosphates, and tributyl phosphates among others; and mixtures thereof.

Especially preferable, are those antifoaming agents or defoamers which are of food grade quality given the application of the method of the invention. To this end, one of the more effective antifoaming agents includes silicones. Silicones such as dimethyl silicone, glycol polysiloxane, methylphenol polysiloxane, trialkyl or tetralkyl silanes, hydrophobic silica defoamers and mixtures thereof can all be used in defoaming applications. Commercial defoamers commonly available include silicones such as Ardefoam® from Armour Industrial Chemical Company which is a silicone bound in an organic emulsion; Foam Kill® or Kresseo® available from Krusable Chemical Company which are silicone and non-silicone type defoamers as well as silicone esters; and Anti-Foam A® and DC-200 from Dow Corning Corporation which are both food grade type silicones among others. These defoamers can be present at a concentration range from about 0.01 wt-% to 5 wt-%, preferably from about 0.01 wt-% to 2 wt-%, and most preferably from about 0.01 wt-% to about 1 wt-%.

Hydrotrope

The poultry wash composition of the invention or employed in the methods of the invention may also include a hydrotrope coupler or solubilizer. Such materials can be used to ensure that the composition remains phase stable and in a single highly active aqueous form. Such hydrotrope solubilizers or couplers can be used at compositions which maintain phase stability but do not result in unwanted compositional interaction.

Representative classes of hydrotrope solubilizers or coupling agents include an anionic surfactant such as an alkyl sulfate, an alkyl or alkane sulfonate, a linear alkyl benzene or naphthalene sulfonate, a secondary alkane sulfonate, alkyl ether sulfate or sulfonate, an alkyl phosphate or phosphonate, dialkyl sulfosuccinic acid ester, sugar esters (e.g., sorbitan esters) and a $C_{8-10}$ alkyl glucoside.

Preferred coupling agents for use in the rinse agents of the invention include n-octane sulfonate and aromatic sulfonates such as an alkyl aryl sulfonate (e.g., sodium xylene sulfonate or naphthalene sulfonate). Many hydrotrope solubilizers independently exhibit some degree of antimicrobial activity at low pH. Such action adds to the efficacy of the invention but is not a primary criterion used in selecting an appropriate solubilizing agent. Since the presence of the peroxycarboxylic acid material in the protonated neutral state provides beneficial biocidal or antimicrobial activity, the coupling agent should be selected not for its independent antimicrobial activity but for its ability to provide effective single phase composition stability in the presence of substantially insoluble peroxycarboxylic acid materials and the more soluble compositions of the invention. Generally, any number of surfactants may be used consistent with the purpose of this constituent.

Anionic surfactants useful with the invention include alkyl carboxylates, linear alkylbenzene sulfonates, paraffin sulfonates and secondary n-alkane sulfonates, sulfosuccinate esters and sulfated linear alcohols.

Zwitterionic or amphoteric surfactants useful with the invention include β-N-alkylaminopropionic acids, n-alkyl-β-iminodipropionic acids, imidazoline carboxylates, n-alkylIletaines, amine oxides, sulfobetaines and sultaines.

Nonionic surfactants useful in the context of this invention are generally polyether (also known as polyalkylene oxide, polyoxyalkylene or polyalkylene glycol) compounds. More particularly, the polyether compounds are generally polyoxypropylene or polyoxyethylene glycol compounds. Typically, the surfactants useful in the context of this invention are synthetic organic polyoxypropylene (PO)-polyoxyethylene (EO) block copolymers. These surfactants have a diblock polymer including an EO block and a PO block, a center block of polyoxypropylene units (PO), and having blocks of polyoxyethylene grated onto the polyoxypropylene unit or a center block of EO with attached PO blocks. Further, this surfactant can have further blocks of either polyoxyethylene or polyoxypropylene in the molecule. The average molecular weight of useful surfactants ranges from about 1000 to about 40,000 and the weight percent content of ethylene oxide ranges from about 10–80% by weight.

Also useful in the context of this invention are surfactants including alcohol alkoxylates having EO, PO and BO blocks. Straight chain primary aliphatic alcohol alkoxylates can be particularly useful as sheeting agents. Such alkoxylates are also available from several sources including BASF Wyandotte where they are known as "Plurafac" surfactants. A particular group of alcohol alkoxylates found to be useful are those having the general formula $R-(EO)_m-(PO)_n$ wherein m is an integer of about 2–10 and n is an integer from about 2–20. R can be any suitable radical such as a straight chain alkyl group having from about 6–20 carbon atoms.

Other useful nonionic surfactants of the invention include capped aliphatic alcohol alkoxylates. These end caps include but are not limited to methyl, ethyl, propyl, butyl, benzyl and chlorine. Useful alcohol alkoxylated include ethylene diamine ethylene oxides, ethylene diamine propylene oxides, mixtures thereof, and ethylene diamine EO-PO compounds, including those sold under the tradename Tetronic. Preferably, such surfactants have a molecular weight of about 400 to 10,000. Capping improves the compatibility between the nonionic and the oxidizers hydrogen peroxide and peroxycarboxylic acid, when formulated into a single composition. Other useful nonionic surfactants are alkylpolyglycosides.

Another useful nonionic surfactant of the invention is a fatty acid alkoxylate wherein the surfactant includes a fatty acid moiety with an ester group including a block of EO, a block of PO or a mixed block or heteric group. The molecular weights of such surfactants range from about 400 to about 10,000, a preferred surfactant has an EO content of about 30 to 50 wt-% and wherein the fatty acid moiety contains from about 8 to about 18 carbon atoms.

Similarly, alkyl phenol alkoxylates have also been found useful in the invention. Such surfactants can be made from an alkyl phenol moiety having an alkyl group with 4 to about 18 carbon atoms, can contain an ethylene oxide block, a propylene oxide block or a mixed ethylene oxide, propylene oxide block or heteric polymer moiety. Preferably such surfactants have a molecular weight of about 400 to about 10,000 and have from about 5 to about 20 units of ethylene oxide, propylene oxide or mixtures thereof.

The concentration of hydrotrope useful in the present invention generally ranges from about 0.1 to about 20 wt-%, preferably from about 0.5 to about 10 wt-%, most preferably from about 1 to about 4 wt-%.

Thickening or Gelling Agents

Thickeners useful in the present invention include those which do not leave contaminating residue on the surface of poultry or poultry processing apparatus. That is, preferred thickeners or gelling agents do not include components incompatible with food or other sensitive products in contact areas.

Generally, thickeners which may be used in the present invention include natural gums such as xanthan gum, guar gum, or other gums from plant mucilage; polysaccharide based thickeners, such as alginates, starches, and cellulosic polymers (e.g., carboxymethyl cellulose); polyacrylates thickeners; and hydrocolloid thickeners, such as pectin. Generally, the concentration of thickener employed in the present compositions or methods will be dictated by the desired viscosity within the final composition. However, as a general guideline, the viscosity of thickener within the present composition ranges from about 0.1 wt-% to about 1.5 wt-%, preferably from about 0.1 wt-% to about 1.0 wt-%, and most preferably from about 0.1 wt-% to about 0.5 wt-%.

Formulation

The compositions of or used in the methods of the invention can be formulated by combining the antimicrobially active materials (e.g., carboxylic acids, peroxycarboxylic acids, and hydrogen peroxide) with adjuvant or other components with the materials that form the antimicrobial composition. The compositions can also be formulated with preformed peroxycarboxylic acids. The preferred compositions of the invention can be made by mixing the carboxylic acid or mixture thereof with an optional hydrotrope solubilizer or coupler, reacting the mixture with hydrogen peroxide and then adding the balance of required ingredients to provide rinsing and antimicrobial action.

A stable equilibrium mixture is produced containing the carboxylic acid or blend with hydrogen peroxide and allowing the mixture to stand for 1–14 days at 15° C. or more. With this preparatory method, an equilibrium mixture will be formed containing an amount of hydrogen peroxide, unoxidized acid, oxidized or peroxycarboxylic acid and unmodified couplers, solubilizer, or stabilizers.

Use Compositions

The invention contemplates a concentrate composition which is diluted to a use solution prior to application to poultry. Primarily for reasons of economics, the concentrate would normally be marketed and an end user would preferably dilute the concentrate with water or an aqueous diluent to a use solution.

The level of active components in the concentrate composition is dependent on the intended dilution factor and the desired activity of the peroxycarboxylic acid compound and the carboxylic acid. Generally, a dilution of about 0.5 to about 20 fluid ounces to about 100 gallons of water is used for aqueous antimicrobial compositions. Higher use dilutions can be employed if elevated use temperature (greater than 25° C.) or extended exposure time (greater than 30 seconds) can be employed. In the typical use locus, the concentrate is diluted with a major proportion of water and used for poultry processing using commonly available tap or service water mixing the materials at a dilution ratio of about 3 to about 20 ounces of concentrate per 100 gallons of water.

Methods Employing Mixed Peroxycarboxylic Acid Compositions

Poultry Processing

The concentrate and use compositions of the present invention can be employed for a variety of antimicrobial purposes, preferably as or for forming water-based systems for processing and/or washing poultry. The present compositions and methods can be employed for processing poultry and/or poultry meat at any step from gathering the live birds through packaging the final product. For example, the present compositions and methods can employed for washing, rinsing, chilling, or scalding poultry carcasses, poultry carcass parts, or poultry organs for reducing contamination of these items with spoilage/decay-causing bacteria, and pathogenic bacteria.

Before processing, live poultry are generally transported to and gathered at the beginning of a processing line. Poultry can be washed before entering the processing line. Processing typically begins with sacrificing the bird, typically by electrical stunning, followed by neck cutting and bleeding. A first washing step, known as scalding (e.g. submersion or immersion scalding) typically follows bleeding and loosens attachment of feathers to poultry skin. Submersion scalding can be accomplished according to the methods and employing compositions of the present invention. Submersion scalding typically includes immersing a stunned and bled bird into a scalding hot bath of water or a liquid antimicrobial composition, typically at a temperature of about 50 to about 80° C., preferably about 50 to about 60° C. The liquid antimicrobial composition in the bath can be agitated, sonicated, or pumped to increase contact of the composition with the carcass. Scalding is generally conducted in a scald tank or trough, which contains the scalding liquid with sufficient liquid depth to completely submerse the poultry carcass. The carcass is generally transported through the tank or trough by conveyor at a speed that provides a few minutes in the scalding liquid.

According to the present invention, the scalding bath can include a mixed peroxycarboxylic acid antimicrobial composition, preferably a composition of the present invention. Preferably, the scalding hot bath contains a peroxycarboxylic acid antimicrobial composition with about 2 to about 50 ppm, preferably about 30 ppm of peroxycarboxylic acid present as a mixture of peroxyacetic acid and peroxyoctanoic acid, and amounts and additional ingredients as described herein. The scalding bath can also include one or more of the additional ingredients permitted in scalding baths.

After submersion scalding, the poultry is typically picked and, optionally, singed before the next washing process. This second washing process is generally known as "dress" rinsing, "New York dress" rinsing, or post-pick rinsing, which rinses residual feathers and follicle residues from the carcass. Dress rinsing typically includes spraying a picked carcass with water, typically at a temperature of about 5 to about 30° C. To increase contact with the carcass, the antimicrobial compositions in the spray water can be applied at higher pressures, flow rates, temperatures, or with agitation or ultrasonic energy. Dress rinsing is typically accomplished with a washing apparatus such as a wash or spray cabinet with stationary or moving spray nozzles. Alternatively, a "flood"-rinsing or liquid submersion washing apparatus may be used immediately after picking.

According to the present invention, dress rinsing can be accomplished employing a peroxycarboxylic acid antimicrobial composition, preferably a composition of the present invention. For example, the dress rinsing can employ a peroxycarboxylic acid antimicrobial composition with about 50 to about 300 ppm, preferably about 200 ppm of peroxycarboxylic acid present as a mixture of peroxyacetic acid and peroxyoctanoic acid, and amounts and additional ingredients as described herein.

Dress rinsing is typically a final washing step before dismembering the poultry. Dismembering can include removing the head, the feet, eviscerating, and removing the neck, in any order commonly employed in poultry processing. The dismembered and eviscerated poultry can then be subjected to a washing step known as inside-outside bird washing (IOBW). Inside-outside bird washing washes the interior (body cavity) and exterior of the bird. Inside-outside bird washing typically includes rinsing the interior and exterior surfaces of the carcass with streams or floods of water, typically at a temperature of about 5 to about 30° C. To increase contact with the carcass, the antimicrobial compositions in the spray water can be applied at higher pressures, flow rates, temperatures, or with agitation or ultrasonic energy. Inside-outside bird washing is generally accomplished by an apparatus that floods the bird carcass with streams of water in the inner cavity and over the exterior of the carcass. Such an apparatus can include a series of fixed spray nozzles to apply antimicrobial composition to the exterior of the bird and a rinse probe or bayonet that enters and applies antimicrobial composition to the body cavity.

According to the present invention, inside-outside bird washing can be accomplished employing a peroxycarboxylic acid antimicrobial composition, preferably a composition of the present invention. For example, inside-outside bird washing can employ a peroxycarboxylic acid antimicrobial composition about 20 to about 200 ppm preferably about 50 to about 100 ppm of peroxycarboxylic acid present as a mixture of peroxyacetic acid and peroxyoctanoic acid, and amounts and additional ingredients as described herein.

After inside-outside bird washing, both the interior and the exterior of the bird can be subjected to further decontamination. This further decontamination can be accomplished in part by a step commonly known as antimicrobial spray rinsing, sanitizing rinsing, or finishing rinsing. Such rinsing typically includes spraying the interior and exterior surfaces of the carcass with water, typically at a temperature of about 5 to about 30° C. To increase contact with the carcass, the antimicrobial compositions in the spray water can be applied using fixed or articulating nozzles, at higher pressures, flow rates, temperatures, with agitation or ultrasonic energy, or with rotary brushes. Spray rinsing is typically accomplished by an apparatus such as a spray cabinet with stationary or moving spray nozzles. The nozzles create a mist, vapor, or spray that contacts the carcass surfaces.

According to the present invention, antimicrobial spray rinsing, sanitizing rinsing, or finishing rinsing can be accomplished employing a peroxycarboxylic acid antimicrobial composition, preferably a composition of the present invention. For example, spray rinsing can employ a peroxycarboxylic acid antimicrobial composition with about 50 to about 300 ppm preferably about 100 to about 200 ppm of peroxycarboxylic acid present as a mixture of peroxyacetic acid and peroxyoctanoic acid, and amounts and additional ingredients as described herein.

After spray rinsing, the bird can be made ready for packaging or for further processing by chilling, specifically submersion chilling or air chilling. Submersion chilling both washes and cools the bird to retain quality of the meat. Submersion chilling typically includes submersing the carcass completely in water or slush, typically at a temperature of less than about 5° C., until the temperature of the carcass approaches that of the water or slush. Chilling of the carcass can be accomplished by submersion in a single bath, or in two or more stages, each of a lower temperature. Water can be applied with agitation or ultrasonic energy to increase contact with the carcass. Submersion chilling is typically accomplished by an apparatus such as a tank containing the chilling liquid with sufficient liquid depth to completely submerse the poultry carcass. The carcass can be conveyed through the chiller by various mechanisms, such as an auger feed or a drag bottom conveyor. Submersion chilling can also be accomplished by tumbling the carcass in a chilled water cascade.

According to the present invention, submersion chilling can be accomplished employing a peroxycarboxylic acid antimicrobial composition, preferably a composition of the present invention. For example, submersion chilling can employ a peroxycarboxylic acid antimicrobial composition with about 2 to about 100 ppm preferably about 2 to about 30 ppm of peroxycarboxylic acid present as a mixture of peroxyacetic acid and peroxyoctanoic acid, and amounts and additional ingredients as described herein.

Like submersion chilling, air chilling or cryogenic chilling cools the bird to retain quality of the meat. Air cooling can be less effective for decontaminating the bird, as the air typically would not dissolve, suspend, or wash away contaminants. Air chilling with a gas including an antimicrobial agent can, however, reduce the burden of microbial, and other, contaminants on the bird. Air chilling typically includes enclosing the carcass in a chamber having a temperature below about 5° C. until the carcass is chilled. Air chilling can be accomplished by applying a cryogenic fluid or gas as a blanket or spray.

According to the present invention, air chilling can be accomplished employing a peroxycarboxylic acid antimicrobial composition, preferably a composition of the present invention. For example, air chilling compositions can include a gaseous or densified fluid antimicrobial composition.

After chilling, the bird can be subjected to additional processing steps including weighing, quality grading, allocation, portioning, deboning, and the like. This further processing can also include methods or compositions according to the present invention for washing with mixed peroxycarboxylic acid compositions. For example, it can be advantageous to wash poultry portions, such as legs, breast quarters, wings, and the like, formed by portioning the bird. Such portioning forms or reveals new meat, skin, or bone surfaces which may be subject to contamination and benefit from treatment with an antimicrobial composition. Similarly, deboning a poultry carcass or a portion of a poultry carcass can expose additional areas of the meat or bone to microbial contamination. Washing the deboned poultry carcass or portion with a mixed peroxycarboxylic acid composition can advantageously reduce any such contamination. In addition, during any further processing, the deboned meat can also come into contact with microbes, for example, on contaminated surfaces. Washing the deboned meat with a mixed peroxycarboxylic acid composition can reduce such contamination. Washing can be accomplished by spraying, immersing, tumbling, or a combination thereof, or by applying a gaseous or densified fluid antimicrobial composition.

Usable side products of poultry include heart, liver, and gizzard (e.g. giblets), neck, and the like. These are typically harvested later in processing, and are sold as food products. Of course, microbial contamination of such food products is undesirable. Thus, these side products can also be washed with a mixed peroxycarboxylic acid composition in methods of the present invention. Typically, these side products will be washed after harvesting from the poultry carcass and before packaging. They can be washed by submersion or spraying, or transported in a flume including the antimicrobial composition. They can be contacted with an antimicrobial composition according to the invention in a giblet chiller or ice chiller.

The poultry, poultry product, poultry portion, poultry side product, or the like can be packaged before sending it to more processing, to another processor, into commerce, or to the consumer. Any such poultry can be washed with a water based mixed peroxycarboxylic acid antimicrobial composition, which can then be removed (e.g., drained, blown, or blotted) from the poultry. In certain circumstances wetting the poultry before packaging is disadvantageous. In such circumstances, a gaseous or densified fluid form of the peroxycarboxylic acid antimicrobial composition can be employed for reducing the microbial burden on the poultry. Such a gaseous composition can be employed in a variety of processes known for exposing poultry to a gas before or during packaging, such as modified atmosphere packaging.

The advantageous stability of mixed peroxycarboxylic acid compositions in such methods, which include the presence of poultry debris or residue, makes these compositions competitive with cheaper, less stable, and potentially toxic chlorinated compounds. Preferred methods of the present invention include agitation or sonication of the use composition, particularly as a concentrate is added to water to make the use composition. Preferred methods include water systems that have some agitation, spraying, or other mixing of the solution. The poultry product can be contacted with the compositions of the invention effective to result in a reduction significantly greater than is achieved by washing with water, or at least a 50% reduction, preferably at least a 90% reduction, preferably at least a 99% reduction in the resident microbial preparation.

The present methods require a certain minimal contact time of the composition with poultry for occurrence of significant antimicrobial effect. The contact time can vary with concentration of the use composition, method of applying the use composition, temperature of the use composition, amount of soil on the poultry, number of microorganisms on the poultry, or the like. Preferably the exposure time is at least about 5 to about 15 seconds.

Spraying Poultry

A preferred method for washing poultry employs a pressure spray of the mixed peroxycarboxylic acid composition. During application of the spray solution on the poultry product, the surface of the poultry product can be moved with mechanical action, preferably agitated, rubbed, brushed, etc. Agitation can be by physical scrubbing of the poultry product, through the action of the spray solution under pressure, through sonication, or by other methods. Agitation increases the efficacy of the spray solution in killing micro-organisms, perhaps due to better exposure of the solution into the crevasses or small colonies containing the micro-organisms. The spray solution, before application, can also be heated to a temperature of about 15 to 20° C., preferably about 20 to 60° C. to increase efficacy.

Application of the material by spray can be accomplished using a manual spray wand application, an automatic spray of poultry product moving along a production line using multiple spray heads to ensure complete contact or other spray means. One preferred automatic spray application involves the use of a spray booth. The spray booth substantially confines the sprayed composition to within the parameter of the booth. The production line moves the poultry product through the entryway into the spray booth in which the poultry product is sprayed on all its exterior surfaces with sprays within the booth. After a complete coverage of the material and drainage of the material from the poultry product within the booth, the poultry product can then exit the booth in a fully treated form. The spray booth can include steam jets that can be used to apply the antimicrobial compositions of the invention. These steam jets can be used in combination with cooling water to ensure that the treatment reaching the poultry product surface is less than 65° C., preferably less than 60° C. The temperature of the spray on the poultry product is important to ensure that the poultry product is not substantially altered (cooked) by the temperature of the spray. The spray pattern can be virtually any useful spray pattern.

Immersing Poultry

During processing of the poultry product, the poultry product can be immersed into a tank containing a quantity of washing solution. The washing solution is preferably agitated to increase the efficacy of the solution and the speed in which the solution reduces micro-organisms accompanying to the poultry product. Agitation can be obtained by conventional methods, including ultrasonics, aeration by bubbling air through the solution, by mechanical methods, such as strainers, paddles, brushes, pump driven liquid jets, or by combinations of these methods. The washing solution can be heated to increase the efficacy of the solution in killing micro-organisms. It is preferable that the poultry product be immersed in the washing solution after the poultry product have been eviscerated and before any cooling process such as a chiller tank or a chill water spray.

Foam Treating Poultry

In another alternative embodiment of the present invention, the poultry product can be treated with a foaming version of the composition. The foam can be prepared by mixing foaming surfactants with the washing solution at time of use. The foaming surfactants can be nonionic, anionic or cationic in nature. Examples of useful surfactant types include, but are not limited to the following: alcohol ethoxylates, alcohol ethoxylate carboxylate, amine oxides, alkyl sulfates, alkyl ether sulfate, sulfonates, quaternary ammonium compounds, alkyl sarcosines, betaines and alkyl amides. The foaming surfactant is typically mixed at time of use with the washing solution. Use solution levels of the foaming agents is from about 50 ppm to about 2.0 wt-%. At time of use, compressed air can be injected into the mixture, then applied to the poultry product surface through a foam application device such as a tank foamer or an aspirated wall mounted roamer.

Gel Treating Poultry

In another alternative embodiment of the present invention, the poultry product can be treated with a thickened or gelled version of the composition. In the thickened or gelled state the washing solution remains in contact with the poultry product surface for longer periods of time, thus increasing the antimicrobial efficacy. The thickened or gelled solution will also adhere to vertical surfaces. The composition or the washing solution can be thickened or gelled using existing technologies such as: xanthan gum, polymeric thickeners, cellulose thickeners or the like. Rod micelle forming systems such as amine oxides and anionic counter ions could also be used. The thickeners or gel forming agents can be used either in the concentrated product or mixing with the washing solution, at time of use. Typical use levels of thickeners or gel agents range from about 100 ppm to about 10 wt-%.

Light Treating Poultry

In another alternative embodiment of the present invention, the poultry product can be exposed to an activating light (or other electromagnetic radiation) source following application of the washing solution. The activating light (or other electromagnetic radiation) can improve the antimicrobial efficacy of the washing solution. The light can be ultraviolet light, infrared light, visible light, or a combination thereof. Other forms of electromagnetic radiation include radar and microwave.

Processing Poultry Wash Water

Washing poultry can employ a large volume of water, or another carrier. Poultry wash water can be used more than once (recycled), provided the water can be treated so that it does not transfer undesirable microbes to the poultry being washed with the recycled wash water. One way to prevent the transfer of such undesirable microbes, is to reduce the microbial burden of the recycled wash water by adding a mixture of peroxycarboxylic acids. For example, if the fluid to be recycled is water-based and lacking any peroxycarboxylic acid, a mixed peroxycarboxylic acid concentrate composition can be added to result in an effective antimicrobial concentration of peroxycarboxylic acid in the fluid to be recycled. Alternatively, if the fluid to be recycled already includes or has included a peroxycarboxylic acid, a mixed peroxycarboxylic acid concentrate composition can be added to increase any concentration of peroxycarboxylic acid to an effective antimicrobial level. It may be that the peroxycarboxylic acid in the solution to be recycled has been totally depleted, in which case more of the mixed peroxycarboxylic acid composition is added.

In some circumstances, the water to be recycled includes a substantial burden of organic matter or microbes. If this is the case, the water may be unsuitable for recycling. However, if the water is to be recycled, the operator adds a sufficient quantity of the mixed peroxycarboxylic acid composition to provide an effective antimicrobial amount of the peroxycarboxylic acid after a certain amount is consumed by the organic burden or microbes already present. Then, the recycled fluid can be used with antimicrobial effect. Routine testing can be employed for determining levels of peroxycarboxylic acid, or of organic burden.

In each case, the method of recycling the poultry wash water includes recovering the poultry wash water, adding a mixed composition of peroxycarboxylic acids, and reusing the poultry wash water for washing poultry, for example, as described above. The poultry wash water can be recovered from steps in poultry processing including submersion scalding, dress rinsing, inside-outside bird washing, spray rinsing, and submersion chilling. Methods of recovering wash water from these steps are well-known to those skilled in the poultry washing and/or processing arts. The wash water can also be strained, filtered, diluted, or otherwise cleaned in processed during recycling.

The present invention may be better understood with reference to the following examples. These examples are intended to be representative of specific embodiments of the invention, and are not intended as limiting the scope of the invention.

EXAMPLES

Example 1

Formulas for Peroxyacetic/Peroxyoctanoic Acid Mixtures Having Activity Against Microbes Contaminating Poultry A preferred antimicrobial concentrate composition of the invention was formulated as:

| Material | Weight - % |
| --- | --- |
| Glacial Acetic Acid | 55 |
| Hydrogen Peroxide | 11 |
| HEDP | 0.6 |
| Octanoic Acid | 4 |

The remainder of this concentrate composition was water.

This concentrate formulation converted to a composition including peroxy acids during storage for two weeks at generally ambient conditions. In this case, the concentrate composition converted to:

| Chemical | Typical Weight Percent of Chemical In Concentrate 2 Weeks Post-Manufacture |
| --- | --- |
| Acetic Acid | 41 |
| Hydrogen Peroxide | 6.2 |
| HEDP | 0.6 |
| Octanoic Acid | 3.2 |
| Peroxyacetic Acid | 12 |
| Peroxyoctanoic Acid | 0.8 |

The remainder of this concentrate composition was water.

Such concentrate compositions were diluted to form use compositions of the present invention, which include:

| Component | Use Solution 1 (ppm) | Use Solution 2 (ppm) | Use Solution 3 (ppm) | Use Solution 4 (ppm) |
| --- | --- | --- | --- | --- |
| Glacial Acetic Acid | 6.8 | 17 | 101 | 985 |
| Deionized water | Balance | Balance | Balance | Balance |
| Peroxyacetic Acid | 2 | 5 | 30 | 213 |
| HEDP | 0.1 | 0.3 | 1.5 | 13 |
| Octanoic Acid | 0.5 | 1.3 | 8 | 74 |

-continued

| Component | Use Solution 1 (ppm) | Use Solution 2 (ppm) | Use Solution 3 (ppm) | Use Solution 4 (ppm) |
|---|---|---|---|---|
| Peroxyoctanoic Acid | 0.1 | 0.3 | 2 | 14 |
| Hydrogen Peroxide | 1.0 | 2.6 | 16 | 110 |

Example 2

Spray Application of a Mixed Peroxycarboxylic Acid Antimicrobial Composition Reduces Bacterial Pathogen Contamination on Poultry Spray application of an antimicrobial composition of the invention was tested and shown to significantly reduce bacterial pathogen contamination on poultry carcass samples.

Materials and Methods

Carcass samples were contaminated with either *Salmonella typhimurium* ATCC 13311, *Escherichia coli* serotype O157:H7 ATCC 43895, or *Listeria monocytogenes* (Petite Scott A) ATCC 49594. Identities of these bacteria were confirmed based on gram stain reactions, microscopic morphology and growth characteristics using the appropriate selective medium. These strains were grown in culture, by conventional techniques, and adjusted to yield $\geq 10^7$ colony forming units per milliliter (CFU/mL).

Carcass samples were prepared by inoculating the exterior of a thawed 2×2 inch square of chicken skin with 1 mL of a pathogen culture. The square of skin was depressed to form a bowl, and the culture was allowed to sit in this bowl for 5 min to allow attachment of the bacteria. After attachment, culture was removed from the skin sample and each sample was placed on a metal stand, epidermal side/inoculated side up.

The skin sample was then sprayed with an antimicrobial composition described in Example 1. For use, the composition was diluted to 200±10 ppm total peroxyacid measured as peroxyacetic acid. The poultry carcass sample was sprayed with the composition for 15 seconds at 60 psi and room temperature.

After spraying, the skin samples were aseptically removed and placed into 20 mL of solution including an agent that inactivates the peroxycarboxylic acids without killing bacteria. The remaining bacteria were suspended by vortexing and serial dilutions of this solution were plated for growth of the bacteria. Dilutions were prepared using phosphate buffered dilution water (PBDW). *S. typhimurium* and *L. monocytogenes* plates were incubated at 37° C. for 48 hours. *E. coli* O157:H7 plates were incubated at 37° C. for 24 hours. For each sample, the number of colony forming units per skin square were calculated.

Results

Statistical analysis of the numbers of bacteria on skin samples demonstrated that spray application of the antimicrobial composition of the invention significantly reduced levels of *Salmonella typhimurium*, *Escherichia coli*, and *Listeria monocytogenes*. These results are illustrated in Table 1 below.

TABLE 1

Log Reduction of Bacteria Levels After Spraying With a Mixed Peroxycarboxylic Acid Antimicrobial Agent

| Bacteria | Peroxycarboxylic Acid Antimicrobial Agent |
|---|---|
| *Salmonella typhimurium* | 0.8 |
| *Escherichia coli* | 3.2 |
| *Listeria monocytogenes* | 2.1 |

Conclusion

Spray application of an antimicrobial composition of the invention significantly reduces bacterial pathogen contamination on poultry carcass samples.

Example 3

Submersion Application of a Mixed Peroxycarboxylic Acid Antimicrobial Composition Reduces Bacterial Pathogen Contamination on Poultry Submersion application of an antimicrobial composition of the invention was tested and shown to significantly reduce bacterial pathogen contamination on poultry carcass samples.

Materials and Methods

Bacteria were selected and cultured generally as described in Example 2 above, except that the bacteria were diluted to $\geq 10^6$ colony forming units per milliliter (CFU/mL) for inoculation of carcass samples.

Carcass samples were prepared by thawing frozen chicken wings and livers. The thawed samples were inoculated by submersing in the suspension of bacteria. Other surfaces were not inoculated. The inoculated surface was marked for identification and allowed to drain and sit for 5 min. at room temperature.

The antimicrobial composition was as described in Example 1. The use solution was diluted to 30 ppm total peroxyacid measured as peroxyacetic acid. Antimicrobial agent was applied by submersing the inoculated and uninoculated surfaces for 60 min in the same 2 liters of a use solution of the antimicrobial agent at 4° C. The same experiment was performed using water without the antimicrobial agent.

After submersing for 60 min., the inoculated and uninoculated surfaces were removed from the antimicrobial agent use solution or water and gently agitated in 100 mL of solution including an agent that inactivates the peroxycarboxylic acids without killing bacteria. Removing and analyzing the uninoculated surfaces was necessary to measure cross contamination of bacteria from the inoculated surfaces. Serial dilutions of this solution were plated for growth of the bacteria as described above in Example 2. Cross contamination log reduction was calculated by subtracting the Log number of bacteria on uninoculated surfaces submersed in the antimicrobial use solution from the Log number of surviving bacteria on uninoculated surfaces submersed in water.

Results

Statistical analysis of the numbers of bacteria on carcass samples demonstrated that submersion application of the antimicrobial composition of the invention significantly reduced levels of Salmonella *typhimurium, Escherichia coli,* and *Listeria monocytogenes*. These results are illustrated in Tables 2 and 3 below.

TABLE 2

Log Reduction of Bacteria Levels After Submersing a
Chicken Wing in a Mixed Peroxycarboxylic Acid Antimicrobial Agent

| Bacteria | Peroxycarboxylic Acid Antimicrobial Agent |
|---|---|
| *Salmonella typhimurium* | 0.3 |
| *Escherichia coli* | 1.2 |
| *Listeria monocytogenes* | 1.3 |

TABLE 3

Log Reduction of Bacteria Levels After Submersing a
Chicken Liver in a Mixed Peroxycarboxylic Acid Antimicrobial Agent

| Bacteria | Peroxycarboxylic Acid Antimicrobial Agent |
|---|---|
| *Salmonella typhimurium* | 0.5 |
| *Escherichia coli* | 0.9 |
| *Listeria monocytogenes* | 0.6 |

Conclusion

Submersion application of an antimicrobial composition of the invention significantly reduces bacterial pathogen contamination on poultry carcass samples.

Example 4

Reduction of Spoilage or Decay Causing Bacteria on Poultry Carcasses

This study determined that a mixed peroxycarboxylic acid antimicrobial composition in water used for spraying or submersing eviscerated chicken carcasses provided a reduction of total aerobic bacteria, coliform bacteria, and *Escherichia coli*.

Materials and Methods

Freshly collected chicken carcasses were subjected to spraying with or submersion in an antimicrobial composition described in Example 1 above. Use solutions, spray time and pressure, and submersion temperature and duration were as described in Examples 2 and 3 above. Some carcasses were both sprayed and submersed. Control carcasses were untreated.

Each carcass was then placed in a collection bag using freshly gloved hands. In the bag, the carcass was rinsed with Butterfield's Phosphate Diluent (BPD) and the BPD solution collected for microbiology testing. Known, standard procedures for quantifying total aerobic bacteria, coliform bacteria, and *Escherichia coli* were employed.

Results

Statistical analysis of the numbers of bacteria on carcass samples demonstrated that spray, submersion, and combination application of the antimicrobial composition of the invention significantly reduced levels of total aerobic bacteria, coliform bacteria, and *Escherichia coli*. These results are illustrated in Table 4 below.

TABLE 4

Log Reduction of Bacteria Levels After Treating a Chicken Carcass
with a Mixed Peroxycarboxylic Acid Antimicrobial Agent

| Application | Aerobic Plate Count | *E. coil* Count | Coliform Count |
|---|---|---|---|
| Spray | 0.62 | 0.84 | 0.64 |
| Submersion | 1.21 | 1.37 | 1.27 |
| Spray and Submersion | 1.33 | 1.44 | 1.31 |

Conclusion

Spray, submersion, and spray and submersion application of an antimicrobial composition of the invention significantly reduces contamination by spoilage or decay causing bacteria on poultry carcasses.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

We claim:

1. A method of reducing a microbial population on poultry during processing comprising:
    applying to the poultry during processing a mixed peroxycarboxylic acid antimicrobial composition in an amount and time sufficient to reduce the microbial population;
    recovering the applied mixed peroxycarboxylic acid antimicrobial composition; and
    adding to the recovered composition a sufficient amount of a mixture of peroxycarboxylic acids to yield a recycled mixed peroxycarboxylic acid antimicrobial composition.

2. The method of claim 1, wherein the poultry being processed comprises chicken, turkey, ostrich, game hen, squab, guinea fowl, pheasant, duck, goose, or emu.

3. The method of claim 1, comprising applying the mixed peroxycarboxylic acid composition by submersing the poultry.

4. The method of claim 3, comprising applying the mixed peroxycarboxylic acid composition by submersion scalding, by submersion chilling, by hydro-cooling or chilling, tumble immersion, or by a combination thereof.

5. The method of claim 3, comprising applying the mixed peroxycarboxylic acid composition for a duration and at a concentration selected to yield visually imperceptible darkening of subcutaneous bruises, pooled blood, or a combination thereof.

6. The method of claim 1, comprising applying the mixed peroxycarboxylic acid composition by rinsing or spraying the poultry.

7. The method of claim 6, comprising applying the mixed peroxycarboxylic acid composition with a de-feathering picker, by inside-outside bird washing, by dress rinsing, by spray rinsing, or a combination thereof.

8. The method of claim 1, comprising applying the mixed peroxycarboxylic acid composition to a whole poultry carcass.

9. The method of claim 8, comprising applying the mixed peroxycarboxylic acid composition to a poultry carcass that has been subjected to stunning, bleeding, scalding, picking, singeing, or a combination thereof.

10. The method of claim 1, comprising applying the mixed peroxycarboxylic acid composition to one or more dismembered parts of a poultry carcass.

11. The method of claim 10, comprising applying the mixed peroxycarboxylic acid composition to a poultry carcass that has been subjected to beheading, removing feet, eviscerating, neck-cropping, portioning, or a combination thereof.

12. The method of claim 11, comprising applying the mixed peroxycarboxylic acid composition to a poultry leg, thigh, breast quarter, wing, or combination thereof of a poultry that has been subjected to portioning.

13. The method of claim 10, comprising applying the mixed peroxycarboxylic acid composition to a poultry that has also been subjected to boning.

14. The method of claim 13, comprising applying the mixed peroxycarboxylic acid composition to a boned poultry leg, thigh, breast, wing, or combination thereof.

15. The method of claim 1, comprising applying the mixed peroxycarboxylic acid composition by air chilling.

16. The method of claim 1, further comprising exposing the poultry to activated light.

17. The method of claim 16, wherein the activated light comprises ultraviolet light, infrared light, visible light, or a combination thereof.

18. The method of claim 1, wherein the mixed peroxycarboxylic acid antimicrobial composition comprises:
at least about 2 ppm of one or more mono- or di-peroxycarboxylic acids having up to 6 carbon atoms; and
at least 0.5 ppm of one or more carboxylic acids having up to 12 carbon atoms.

19. The method of claim 18, wherein the mixed peroxycarboxylic acid composition comprises one or more peroxycarboxylic acids having from 2 to 6 carbon atoms and a peroxycarboxylic acid having from 7 to 12 carbon atoms.

20. The method of claim 19, wherein the mixed peroxycarboxylic acid composition comprises peroxyacetic acid and peroxyoctanoic acid.

21. The method of claim 20, wherein the mixed peroxycarboxylic acid antimicrobial composition further comprises stabilizing agent, wetting agent, hydrotrope, thickener, foaming agent, acidifier, pigment, dye, surfactant, or a combination thereof.

22. The method of claim 1, wherein the microbial population is the result of contamination by fecal matter or digestive tract content.

23. The method of claim 22, wherein the microbial population is reduced in a continuous online process.

24. The method of claim 1, further comprising applying the recycled composition to poultry during processing.

25. The method of claim 1, wherein the mixture of peroxycarboxylic acids comprises peroxyacetic acid and peroxyoctanoic acid.

26. The method of claim 25, wherein the mixture of peroxycarboxylic acids comprises about 30 to about 60 weight-% acetic acid, about 1 to about 15 weight-% octanoic acid, about 2 to about 12 weight-% hydrogen peroxide, about 6 to about 16 weight-% peroxyacetic acid, and about 0.1 to about 5 weight-% peroxyoctanoic acid, and about 0.1 to about 2 weight-% chelating agent.

27. The method of claim 1, wherein the recycled mixed peroxycarboxylic acid antimicrobial composition comprises:
at least about 2 ppm of one or more mono- or di-peroxycarboxylic acids having up to 6 carbon atoms; and
at least 0.5 ppm of one or more carboxylic acids having up to 12 carbon atoms.

28. The method of claim 27, wherein the recycled mixed peroxycarboxylic acid composition comprises one or more peroxycarboxylic acids having from 2 to 6 carbon atoms and a peroxycarboxylic acid having from 7 to 12 carbon atoms.

29. The method of claim 1, further comprising diluting an antimicrobial concentrate composition to yield the mixed peroxycarboxylic acid antimicrobial composition.

30. The method of claim 29, wherein the antimicrobial concentrate composition comprises:
about 30 to about 60 weight-% acetic acid;
about 1 to about 15 weight-% octanoic acid;
about 2 to about 12 weight-% hydrogen peroxide;
about 6 to about 16 weight-% peroxyacetic acid;
about 0.1 to about 5 weight-% peroxyoctanoic acid; and
about 0.1 to about 2 weight-% chelating agent.

31. The method of claim 30, wherein the antimicrobial concentrate composition further comprises stabilizing agent, wetting agent. hydrotrope, thickener, foaming agent, acidifier, pigment, dye, surfactant, or a combination thereof.

32. The method of claim 30, wherein the antimicrobial concentrate composition comprises:
about 40 weight-% acetic acid;
about 3 weight-% octanoic acid;
about 6 weight-% hydrogen peroxide;
about 10 weight-% peroxyacetic acid;
about 0.8 weight-% peroxyoctanoic acid; and
about 0.6 weight-% chelating agent.

33. The method of claim 29, wherein the antimicrobial concentrate composition comprises:
an equilibrium mixture resulting from a composition comprising:
about 40 to about 70 weight-% acetic acid;
about 2 to about 20 weight-% octanoic acid.
about 5 to about 15 weight-% hydrogen peroxide; and
about 0.3 to about 1 weight-% chelating agent.

34. The method of claim 33, wherein the antimicrobial concentrate composition comprises:
an equilibrium mixture resulting from a composition comprising:
about 55 weight-% acetic acid;
about 11 weight-% hydrogen peroxide;
about 0.6 weight-% chelating agent; and
about 4 weight-% octanoic acid.

35. The method of claim 33, wherein the antimicrobial concentrate composition further comprises stabilizing agent, wetting agent, hydrotrope, thickener, foaming agent, acidifier, pigment, dye, surfactant, or a combination thereof.

36. The method of claim 1, wherein the mixed peroxycarboxylic acid antimicrobial composition comprises:
about 5 to about 1000 ppm acetic acid;
about 0.5 to about 100 ppm octanoic acid;
about 1 to about 200 ppm hydrogen peroxide;

about 2 to about 300 ppm peroxyacetic acid;

about 0.1 to about 20 ppm peroxyoctanoic acid; and about 3 to about 30 ppm chelating agent.

37. The method of claim 36, wherein the mixed peroxycarboxylic acid antimicrobial compostion further comprises stabilizing agent, wetting agent, hydrotrope, thickener, foaming agent, acidifier, pigment, dye, surfactant, or a combination thereof.

38. A method of reducing a microbial population on poultry during processing comprising:

sacrificing the poultry; removing feathers from the sacrificed poultry; removing head, feet, neck, or more than one of head, neck, and feet from the defeathered poultry; eviscerating the defeathered poultry; inside-outside bird washing the eviscerated poultry;

spraying the inside-outside bird washed poultry with a mixed peroxycarboxylic acid antimicrobial composition in an amount and time sufficient to reduce the microbial population;

chilling the peroxycarboxylic acid treated poultry.

39. The method of claim 38, wherein the microbial population is the result of contamination by fecal matter or digestive tract content.

40. The method of claim 39, wherein the microbial population is reduced in a continuous online process.

41. The method of claim 38, wherein chilling comprises submersing the poultry in a chilled mixed peroxycarboxylic acid composition.

42. A method of reducing a microbial population on poultry during processing comprising submersing the poultry in a chilled mixed peroxycarboxylic acid composition.

* * * * *

UNITED STATES PATENT AND TRADEMARK OFFICE
CERTIFICATE OF CORRECTION

PATENT NO. : 6,514,556 B2
DATED : February 4, 2003
INVENTOR(S) : Hilgren et al.

It is certified that error appears in the above-identified patent and that said Letters Patent is hereby corrected as shown below:

<u>Title page,</u>
Item [56], References Cited, U.S. PATENT DOCUMENTS, please insert following:

| | | |
|---|---|---|
| 2,512,640 | 06/27/1950 | Greenspan et al. |
| 3,122,417 | 02/25/1964 | Blaser et al. |
| 3,248,281 | 04/26/1966 | Goodenough |
| 3,350,265 | 10/31/1967 | Rubinstein et al. |
| 3,514,278 | 05/26/1970 | Brink |
| 3,895,116 | 07/15/1975 | Herting et al. |
| 3,996,386 | 12/07/1976 | Malkki et al. |
| 4,041,149 | 08/09/1977 | Gaffar et al. |
| 4,051,058 | 09/27/1977 | Böwing et al. |
| 4,051,059 | 09/27/1977 | Böwing et al. |
| 4,129,517 | 12/12/1978 | Eggensperger, et al. |
| 4,191,660 | 03/04/1980 | Schreiber et al. |
| 4,244,884 | 01/13/1981 | Hutchins et al. |
| 4,370,199 | 01/25/1983 | Orndorff |
| 4,404,040 | 09/13/1983 | Wang |
| 4,477,438 | 10/16/1984 | Willcockson, deceased et al. |
| 4,478,683 | 10/23/1984 | Orndorff |
| 4,501,681 | 02/26/1985 | Groult et al. |
| 4,529,534 | 07/16/1985 | Richardson |
| 4,557,898 | 12/10/1985 | Greene et al. |
| 4,592,488 | 06/03/1986 | Simon et al. |
| 4,613,452 | 09/23/1986 | Sanderson |
| 4,655,781 | 04/07/1987 | Hsieh et al. |
| 4,715,980 | 12/29/1987 | Lopes et al. |
| 4,738,840 | 04/19/1988 | Simon et al. |
| 4,802,994 | 02/07/1989 | Mouché et al. |
| 4,865,752 | 09/12/1989 | Jacobs |
| 4,900,721 | 02/13/1990 | Bansemir et al. |
| 4,906,617 | 03/06/1990 | Jacquet et al. |
| 4,908,306 | 03/13/1990 | Lorincz |
| 4,917,815 | 04/17/1990 | Beilfuss et al. |
| 4,923,677 | 05/08/1990 | Simon et al. |
| 4,937,066 | 06/26/1990 | Vlock |
| 4,943,414 | 07/24/1990 | Jacobs et al. |
| 4,945,110 | 07/31/1990 | Brokken et al. |
| 4,996,062 | 02/26/1991 | Lehtonen et al. |
| 4,997,571 | 03/05/1991 | Roensch et al. |
| 4,997,625 | 03/05/1991 | Simon et al. |
| 5,004,760 | 04/02/1991 | Patton et al. |
| 5,010,109 | 04/23/1991 | Inoi |
| 5,015,408 | 05/14/1991 | Reuss |
| 5,043,176 | 08/27/1991 | Bycroft et al. |
| 5,069,286 | 12/03/1991 | Roensch et al. |
| 5,084,239 | 01/28/1992 | Moulton et al. |
| 5,093,140 | 03/03/1992 | Watanabe |
| 5,114,178 | 05/19/1992 | Baxter |
| 5,114,718 | 05/19/1992 | Damani |
| 5,122,538 | 06/16/1992 | Lokkesmoe et al. |
| 5,129,824 | 07/14/1992 | Keller |

UNITED STATES PATENT AND TRADEMARK OFFICE
CERTIFICATE OF CORRECTION

PATENT NO. : 6,514,556 B2
DATED : February 4, 2003
INVENTOR(S) : Hilgren et al.

It is certified that error appears in the above-identified patent and that said Letters Patent is hereby corrected as shown below:

U.S. PATENT DOCUMENTS cont'd,

| | | |
|---|---|---|
| 5,130,124 | 07/14/1992 | Merianos et al. |
| 5,139,788 | 08/18/1992 | Schmidt |
| 5,176,899 | 01/05/1993 | Montgomery |
| 5,200,189 | 04/06/1993 | Oakes et al. |
| 5,208,057 | 05/04/1993 | Greenley et al. |
| 5,234,703 | 08/10/1993 | Guthery |
| 5,234,719 | 08/10/1993 | Richter et al. |
| 5,268,003 | 12/07/1993 | Coope et al. |
| 5,292,447 | 03/08/1994 | Venturello et al. |
| 5,314,687 | 05/24/1994 | Oakes et al. |
| 5,336,500 | 08/09/1994 | Richter et al. |
| 5,364,650 | 11/15/1994 | Guthery |
| 5,391,324 | 02/21/1995 | Reinhardt et al. |
| 5,409,713 | 04/25/1995 | Lokkesmoe et al. |
| 5,419,908 | 05/30/1995 | Richter et al. |
| 5,435,808 | 07/25/1995 | Holzhauer et al. |
| 5,436,008 | 07/25/1995 | Richter et al. |
| 5,437,868 | 08/01/1995 | Oakes et al. |
| 5,489,434 | 02/06/1996 | Oakes et al. |
| 5,494,588 | 02/27/1996 | LaZonby |
| 5,508,046 | 04/16/1996 | Cosentino et al. |
| 5,512,309 | 04/30/1996 | Bender et al. |
| 5,527,898 | 06/18/1996 | Bauer et al. |
| 5,578,134 | 11/26/1996 | Lentsch et al. |
| 5,591,706 | 01/07/1997 | Ploumen |
| 5,595,967 | 01/21/1997 | Miracle et al. |
| 5,597,790 | 01/28/1997 | Thoen |
| 5,616,335 | 04/01/1997 | Nicolle et al. |
| 5,616,616 | 04/01/1997 | Hall et al. |
| 5,632,676 | 05/27/1997 | Kurschner et al. |
| 5,641,530 | 06/24/1997 | Chen |
| 5,656,302 | 08/12/1997 | Cosentino et al. |
| 5,658,467 | 08/19/1997 | LaZonby et al. |
| 5,674,538 | 10/07/1997 | Lokkesmoe et al. |
| 5,674,828 | 10/07/1997 | Knowlton et al. |
| 5,683,724 | 11/04/1997 | Hei et al. |
| 5,712,239 | 01/27/1998 | Knowlton et al. |
| 5,718,910 | 02/17/1998 | Oakes et al. |
| 5,756,139 | 05/26/1998 | Harvey et al. |
| 5,785,867 | 07/28/1998 | LaZonby et al. |
| 5,840,343 | 11/24/1998 | Hall et al. |
| 5,851,483 | 12/22/1998 | Nicolle et al. |
| 5,891,392 | 04/06/1999 | Monticello et al. |
| 5,900,256 | 05/04/1999 | Scoville, Jr. et al. |
| 5,902,619 | 05/11/1999 | Rubow et al. |
| 5,968,539 | 10/19/1999 | Beerse et al. |
| 5,989,611 | 11/23/1999 | Stemmler, Jr. et al. |
| 6,010,729 | 01/04/2000 | Gutzmann et al. |
| 6,024,986 | 02/15/2000 | Hei |
| 6,033,705 | 03/07/2000 | Isaacs |
| 6,049,002 | 04/11/2000 | Mattila et al. |
| 6,096,226 | 08/01/2000 | Fuchs et al. |
| 6,096,266 | 08/01/2000 | Duroselle |
| 6,096,348 | 08/01/2000 | Miner et al. |

UNITED STATES PATENT AND TRADEMARK OFFICE
CERTIFICATE OF CORRECTION

PATENT NO. : 6,514,556 B2
DATED : February 4, 2003
INVENTOR(S) : Hilgren et al.

It is certified that error appears in the above-identified patent and that said Letters Patent is hereby corrected as shown below:

FOREIGN PATENT DOCUMENTS, insert the following:

| | | |
|---|---|---|
| 35 43 500 A1 | 06/11/1987 | DE |
| 0 195 619 A2 | 09/24/1986 | EP |
| 0 233 731 A2 | 08/26/1987 | EP |
| 0 461 700 A1 | 12/18/1991 | EP |
| 0 569 066 A1 | 11/10/1993 | EP |
| 2 321 301 A | 03/18/1977 | FR |
| 2 324 626 A | 04/15/1977 | FR |
| 78 568 A | 04/20/1978 | LU |
| WO 95/34537 | 12/21/1995 | PCT |
| WO 98/28267 | 07/02/1998 | PCT |

OTHER PUBLICATIONS, insert the following:

Bell, K. et al., "Reduction of foodborne micro-organisms on beef carcass tissue using acetic acid, sodium bicarbonate, and hydrogen peroxide spray washes", *Food Microbiology*, Vol. 14, pp. 439-448 (1997).

UNITED STATES PATENT AND TRADEMARK OFFICE
CERTIFICATE OF CORRECTION

PATENT NO. : 6,514,556 B2
DATED : February 4, 2003
INVENTOR(S) : Hilgren et al.

It is certified that error appears in the above-identified patent and that said Letters Patent is hereby corrected as shown below:

OTHER PUBLICATIONS cont'd,

Eggensperger, H., "Disinfectants Based on Peracid-Splitting Compounds", *Zbl. Bakt. Hyg.*, I. Abt. Orig. B 168, pp. 517-524 (1979).
Lion C. et al., "New decontaminants. Reaction of peroxyacid esters with toxic insecticides", *Bull. Soc. Chim. Belg.*, Vol. 100, No. 7, pp. 555-559 (1991).
Merka, V. et al., "Disinfectant properties of some peroxide compounds.", Abstract No. 67542e, *Chemical Abstracts*, Vol. 67 (1967).
Mulder, R.W.A.W. et al., "Research Note: Salmonella Decontamination of Broiler Carcasses with Lactic Acid, L-Cysteine, and Hdrogen Peroxide", *Poultry Science*, Vol. 66, pp. 1555-1557 (1987).
Parker, W. et al., "Peroxides. II. Preparation, Characterization and Polarographic Behavior of Longchaing Aliphatic Peracids", *Synthesis and Properties of LongChain Aliphatic Peracids*, Vol. 77, pp. 4037-4041 (August 5, 1955).
Parker, W. et al., "Peroxides. IV. Aliphatic Diperacids", *Aliphatic Diperacids*, Vol. 79, pp. 1929-1931 (April 20, 1957).
Towle, G. et al., "Industrial Gums polysaccharides and Their Derivatives", Second Edition, Ch. XIX, "Pectin", pp. 429-444 (year unknown).
Armak Chemicals, "NEO-FAT Fatty Acids", *Akzo Chemicals Inc.*, Bulletin No. 86-17 (1986).
Computer search results - Level 1 - 5 patents (March 1994).
Computer search results from Ecolab Information Center (June 1998).
"Emery® Fatty and Dibasic Acids Specifications and Characteristics", *Emery Industries*, Bulletin 145, (October 1983).
Pfizer Chemical Division, "Pfizer Flocon® Biopolymers for Industrial Uses (xanthan broths)", Data Sheet 679, pp. 1-4 (year unknown).

Signed and Sealed this

Twenty-first Day of October, 2003

JAMES E. ROGAN
*Director of the United States Patent and Trademark Office*